United States Patent
Ellingson (10) Patent No.: US 8,805,496 B2
(45) Date of Patent: Aug. 12, 2014

(54) AUTOMATIC DISABLEMENT OF AN EXPOSURE MODE OF AN IMPLANTABLE MEDICAL DEVICE

(75) Inventor: Michael L. Ellingson, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 846 days.

(21) Appl. No.: 12/362,780

(22) Filed: Jan. 30, 2009

(65) Prior Publication Data

US 2010/0198310 A1 Aug. 5, 2010

(51) Int. Cl.
 *A61N 1/00* (2006.01)
 *A61B 5/05* (2006.01)
 *A61B 5/04* (2006.01)

(52) U.S. Cl.
 USPC ............... 607/6; 607/9; 600/411; 600/509

(58) Field of Classification Search
 USPC ............ 607/9, 27–28, 4–5, 6; 600/411, 509
 See application file for complete search history.

(56) References Cited

U.S. PATENT DOCUMENTS

| | | | |
|---|---|---|---|
| 3,678,937 A | 7/1972 | Cole et al. | |
| 4,091,818 A | 5/1978 | Brownlee et al. | |
| 5,438,990 A | 8/1995 | Wahlstrand et al. | |
| 5,529,578 A | 6/1996 | Struble | |
| 5,697,958 A | 12/1997 | Paul et al. | |
| 6,198,972 B1 | 3/2001 | Hartlaub et al. | |
| 6,348,070 B1 | 2/2002 | Teissl et al. | |
| 6,580,947 B1 | 6/2003 | Thompson | |
| 6,662,050 B2 | 12/2003 | Olson | |
| 6,901,292 B2 | 5/2005 | Hrdlicka et al. | |
| 6,925,328 B2 | 8/2005 | Foster et al. | |
| 6,937,906 B2 | 8/2005 | Terry et al. | |
| 7,047,074 B2 | 5/2006 | Connelly et al. | |
| 7,076,283 B2 | 7/2006 | Cho et al. | |
| 7,082,328 B2 | 7/2006 | Funcke | |
| 7,242,981 B2 | 7/2007 | Ginggen | |
| 7,450,996 B2 | 11/2008 | MacDonald et al. | |
| 8,014,867 B2 * | 9/2011 | Cooke et al. | 607/31 |
| 2003/0144704 A1 | 7/2003 | Terry et al. | |
| 2003/0144705 A1 * | 7/2003 | Funke | 607/27 |
| 2004/0088012 A1 | 5/2004 | Kroll et al. | |
| 2005/0038482 A1 | 2/2005 | Yonce et al. | |
| 2006/0167496 A1 | 7/2006 | Nelson et al. | |
| 2006/0173295 A1 | 8/2006 | Zeijlemaker | |
| 2006/0293591 A1 | 12/2006 | Wahlstrand et al. | |
| 2007/0173890 A1 | 7/2007 | Armstrong | |
| 2007/0238975 A1 | 10/2007 | Zeijlemaker | |
| 2010/0087892 A1 * | 4/2010 | Stubbs et al. | 607/28 |
| 2010/0106227 A1 * | 4/2010 | Min et al. | 607/63 |

FOREIGN PATENT DOCUMENTS

| | | |
|---|---|---|
| EP | 1493460 | 1/2005 |
| WO | WO 2005035048 | 4/2005 |
| WO | WO 2006081434 | 8/2006 |
| WO | WO 2007117835 | 10/2007 |

* cited by examiner

*Primary Examiner* — Catherine Voorhees
(74) *Attorney, Agent, or Firm* — Michael J. Ostrom (57) ABSTRACT

Techniques may automatically disable an exposure mode that was enabled for operation in the presence of a disruptive energy field. For example, an implantable medical device (IMD) automatically disables the exposure operating mode when (i) the amount of time that has elapsed since enabling the IMD exceeds a threshold amount of time and (ii) a disruptive energy field is detected before the amount of time exceeds the threshold amount of time and the disruptive energy field is not currently detected. When either of these conditions is not met, the IMD continues to operate in accordance with the exposure operating mode.

31 Claims, 5 Drawing Sheets

AUTOMATIC DISABLEMENT OF AN EXPOSURE MODE OF AN IMPLANTABLE MEDICAL DEVICE

TECHNICAL FIELD

The disclosure relates generally to implantable medical devices and, in particular, to operation of an implantable medical device in a disruptive energy field.

BACKGROUND

A wide variety of implantable medical devices (IMDs) that deliver a therapy or monitor a physiologic condition of a patient have been clinically implanted or proposed for clinical implantation in patients. IMDs may deliver therapy or monitor conditions with respect to a variety of organs, nerves, muscles or tissues of the patients, such as the heart, brain, stomach, spinal cord, pelvic floor, or the like. In some cases, IMDs may deliver electrical stimulation therapy via one or more electrodes, which may be included as part of one or more elongated implantable medical leads.

For example, an implantable cardiac device, such as a cardiac pacemaker or implantable cardioverter-defibrillator, provides therapeutic stimulation to the heart by delivering electrical therapy signals such as pulses or shocks for pacing, cardioversion, or defibrillation via electrodes of one or more implantable leads. As another example, a neurostimulator may deliver electrical therapy signals, such as pulses, to a spinal cord, brain, pelvic floor or the like, to alleviate pain or treat symptoms of any of a number of neurological or other diseases, such as epilepsy, gastroparesis, Alzheimer's, depression, obesity, incontinence and the like.

Exposure of the IMD to a disruptive energy field may result in improper operation of the IMD. The IMD may be exposed to the disruptive energy field for any of a number of reasons. For example, one or more medical procedures may need to be performed on the patient within which the IMD is implanted. For example, the patient may need to have a magnetic resonance imaging (MRI) scan, computed tomography (CT) scan, electrocautery, diathermy or other medical procedure that produces a magnetic field, electromagnetic field, electric field or other disruptive energy field.

The disruptive energy field may induce energy on one or more of the implantable leads coupled to the IMD. The IMD may inappropriately detect the induced energy on the leads as physiological signals. Alternatively, or additionally, the induced energy on the leads may result in the inability to correctly detect physiological signals. In either case, detection of the induced energy on the leads as physiological signals may result in the IMD delivering therapy when it is not desired or withholding therapy when it is desired. In other instances, the induced energy on the leads may result in stimulation or heating of the tissue and/or nerve site adjacent to the electrodes of the leads. Such heating may result in thermal damage to the tissue, thus compromising pacing and sensing thresholds at the site.

SUMMARY

In general, this disclosure relates to operation of an implantable medical device (IMD) in a disruptive energy field. In particular, this disclosure describes techniques for automatically disabling an exposure mode that was enabled for operation in the presence of a disruptive energy field. In one example, the IMD automatically disables the exposure operating mode when (i) the amount of time that has elapsed since enabling the IMD exceeds a threshold amount of time and (ii) a disruptive energy field is detected before the amount of time exceeds the threshold amount of time and the disruptive energy field is not currently detected. In other words, the IMD may configure itself from the exposure operating mode to a normal operating mode that has increased functionality.

By requiring that both of these conditions are met before disabling the exposure operating mode, the IMD may automatically reconfigure itself back to the normal operating mode without manual programming by a user while preventing the exposure operating mode from being disabled before the patient has actually undergone the MRI scan or is currently undergoing the MRI scan. When either of conditions (i) or (ii) is not met, the IMD continues to operate in accordance with the exposure operating mode.

In one example, this disclosure is directed to a method comprising configuring an implantable medical device from a first operating mode to a second operating mode that is less susceptible to undesirable operation in a disruptive energy field than the first operating mode. The method also comprises setting a timing mechanism to track an amount of time that has elapsed since configuring the implantable medical device from the first operating mode to the second operating mode and monitoring for presence of the disruptive energy field. Additionally, the method comprises automatically configuring the implantable medical device from the second operating mode to the first operating mode when (i) the amount of time that has elapsed since configuring the implantable medical device from the first operating mode to the second operating mode exceeds a threshold amount of time and (ii) the disruptive energy field was detected before the amount of time exceeds the threshold amount of time and the disruptive energy field is not currently detected.

In another example, this disclosure is directed to an implantable medical device comprising means for configuring the implantable medical device from a first operating mode to a second operating mode that is less susceptible to undesirable operation in a disruptive energy field than the first operating mode, means for tracking an amount of time that has elapsed since configuring the implantable medical device from the first operating mode to the second operating mode and means for monitoring for presence of the disruptive energy field. The configuring means of the device automatically configures the implantable medical device from the second operating mode to the first operating mode when (i) the amount of time that has elapsed since configuring the implantable medical device from the first operating mode to the second operating mode exceeds a threshold amount of time and (ii) the disruptive energy field was detected before the amount of time exceeds the threshold amount of time and the disruptive energy field is not currently detected.

In a further example, this disclosure is directed to an implantable medical device comprising a processor that configures the implantable medical device from a first operating mode to a second operating mode that is less susceptible to undesirable operation in a disruptive energy field than the first operating mode, a timing mechanism to track an amount of time that has elapsed since configuring the implantable medical device from the first operating mode to the second operating mode and a disruptive field detector to monitor for presence of the disruptive energy field. The processor automatically configures the implantable medical device from the second operating mode to the first operating mode when (i) the amount of time that has elapsed since configuring the implantable medical device from the first operating mode to the second operating mode exceeds a threshold amount of time and (ii) the disruptive energy field was detected before the amount of time exceeds the threshold amount of time and the disruptive energy field is not currently detected.

In another example, this disclosure is directed to a computer-readable medium comprising instructions that, when executed, cause an implantable medical device to configure the implantable medical device from a first operating mode to a second operating mode that is less susceptible to undesirable operation in a disruptive energy field than the first operating mode, set a timing mechanism to track an amount of time that has elapsed since configuring the implantable medical device from the first operating mode to the second operating mode, and monitor for presence of the disruptive energy field. The computer-readable medium also includes instructions that, when executed, cause the implantable medical device automatically configure the implantable medical device from the second operating mode to the first operating mode when (i) the amount of time that has elapsed since configuring the implantable medical device from the first operating mode to the second operating mode exceeds a threshold amount of time and (ii) the disruptive energy field was detected before the amount of time exceeds the threshold amount of time and the disruptive energy field is not currently detected.

The details of one or more examples are set forth in the accompanying drawings and the description below. Other features, objects, and advantages will be apparent from the description and drawings, and from the statements provided below.

DETAILED DESCRIPTION

Figure 1:
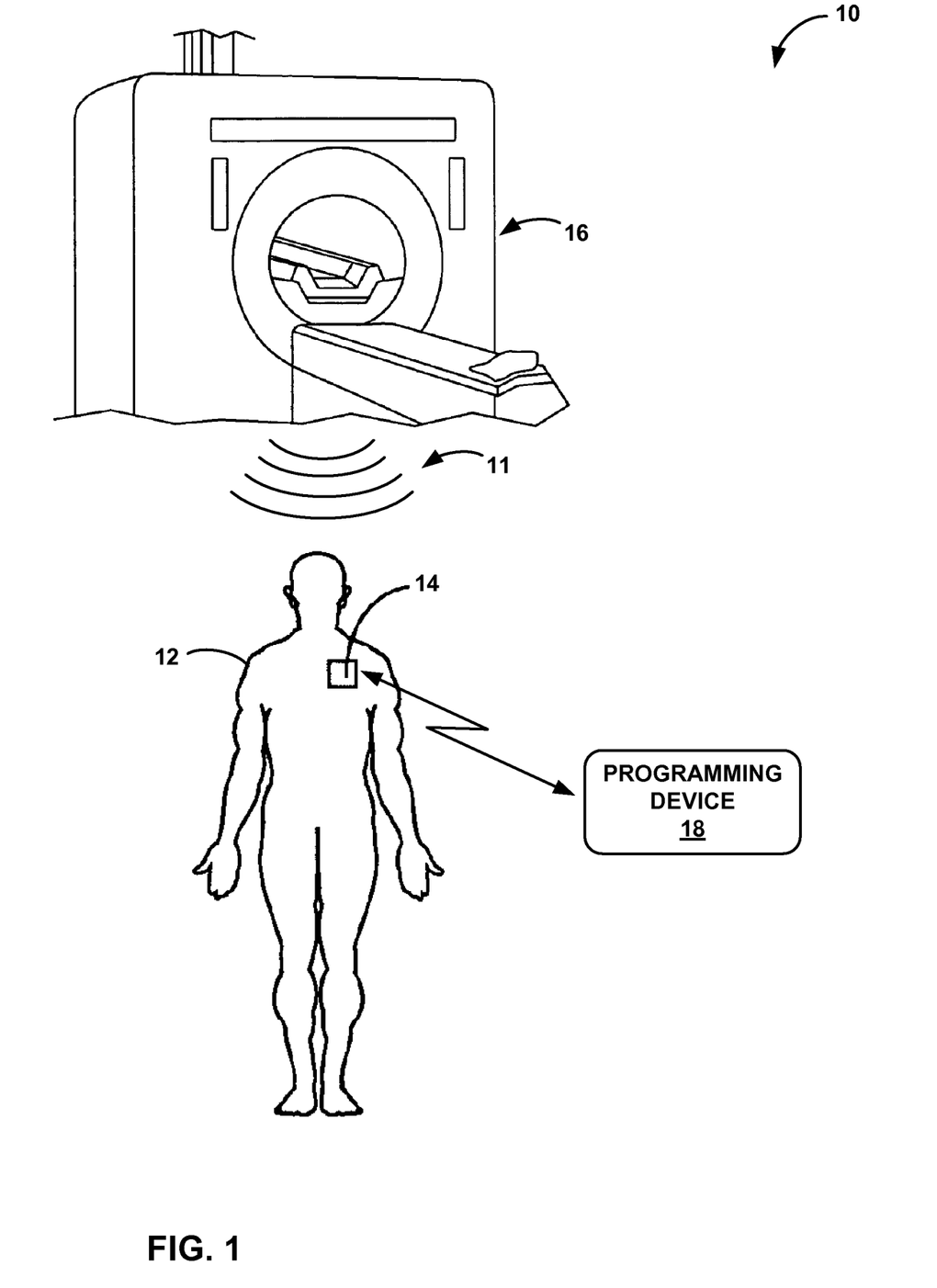
FIG. 1 is a conceptual diagram illustrating an environment in which an implantable medical device is exposed to a disruptive energy field.

FIG. 1 is a conceptual diagram illustrating an environment 10 in which an implantable medical device (IMD) 14 is exposed to a disruptive energy field 11. IMD 14 is implanted within patient 12 to provide therapy to or to monitor a physiological condition of patient 12. Patient 12 ordinarily, but not necessarily, will be a human.

IMD 14 may be any of a variety of therapy devices. For example, IMD 14 may be a device that provides electrical stimulation therapy via one or more implantable leads that include one or more electrodes (not shown). In some instances, IMD 14 may be a device that provides electrical stimulation therapy in the form of cardiac rhythm management therapy to a heart of patient 12 via leads implanted within one or more atria and/or ventricles of the heart. The cardiac rhythm management therapy delivered by IMD 14 may include pacing, cardioversion, defibrillation and/or cardiac resynchronization therapy (CRT). In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like.

In addition to providing electrical stimulation therapy, IMD 14 may sense one or more physiological parameters of patient 12. When one or more leads are implanted within the heart of patient 12, for example, electrodes of the leads may sense electrical signals attendant to the depolarization and repolarizatoin of the heart to monitor a rhythm of the heart or detect particular heart conditions, e.g., tachycardia, bradycardia, fibrillation or the like. IMD 14 may sense a variety of other physiologic parameters or other parameters related to a condition of patient 12, including, for example, neurologic parameters, intracardiac or intravascular pressure, activity, posture, pH of blood or other bodily fluids or the like.

In other instances, IMD 14 may be a device that delivers a drug or therapeutic agent to patient 12 via a catheter. IMD 14 may deliver, e.g., using a pump, the drug or therapeutic agent to a specific location of patient 12. IMD 14 may deliver the drug or therapeutic agent at a constant or variable flow rate. Drug pumps, infusion pump or drug delivery devices may be used to treat symptoms of a number of different conditions. For example, IMD 14 may deliver morphine or ziconotide to reduce or eliminate pain, baclofen to reduce or eliminate spasticity, chemotherapy to treat cancer, or any other drug or therapeutic agent (including saline, vitamins, etc.) to treat any other condition and/or symptom of a condition.

Environment 10 includes an energy source that generates disruptive energy field 11 to which IMD 14 is exposed. In the example illustrated in FIG. 1, the energy source is a MRI scanner 16. Although the techniques of this disclosure are described with respect to disruptive energy field 11 generated by MRI scanner 16, the techniques may be used to control operation of IMD 14 within environments in which other types of disruptive energy fields are present. For example, IMD 14 may operate in accordance with the techniques of this disclosure in environments in with disruptive energy field 11 is generated by a CT scanner, X-ray machine, electrocautery device, diathermy device, ablation device, radiation therapy device, electrical therapy device, magnetic therapy device or any other environment with devices that radiate energy to produce magnetic, electromagnetic, electric fields or other disruptive energy fields.

MRI scanner 16 uses magnetic and radio frequency (RF) fields to produce images of body structures for diagnosing injuries and/or disorders. In particular, MRI scanner 16 generates a static magnetic field, gradient magnetic fields and/or RF fields. The static magnetic field is a non-varying magnetic field that is typically always present around MRI scanner 16 whether or not a MRI scan is in progress. Gradient magnetic fields are low-frequency pulsed magnetic fields that are typically only present while the MRI scan is in progress. RF fields are pulsed RF fields that are also typically only present while the MRI scan is in progress.

Some or all of the various types of fields produced by MRI scanner 16 may interfere with operation of IMD 14. In other words, one or more of the various types of fields produced by MRI scanner 16 may make up disruptive energy field 11. For example, the gradient magnetic and RF fields produced by MRI scanner 16 may induce energy on one or more of the implantable leads coupled to IMD 14. In some instances, IMD 14 inappropriately detects the induced energy on the leads as physiological signals, which may in turn cause IMD 14 to deliver undesired therapy or withhold desired therapy. This inappropriate detection is sometimes referred to as oversensing. In other instances, the induced energy on the leads result in IMD 14 not detecting physiological signals that are actually present, which may again result in IMD 14 delivering undesired therapy or withholding desired therapy. The induced energy on the leads may also result in stimulation or heating of the tissue and/or nerve site adjacent to electrodes of leads extending from IMD 14. Such heating may cause thermal damage to the tissue adjacent the electrodes, possibly compromising pacing and sensing thresholds at the site.

To reduce the undesirable effects of disruptive energy field 11, IMD 14 is capable of operating in a mode that is less susceptible to undesirable operation during exposure to disruptive energy field 11, referred to herein as the "exposure mode" or "exposure operating mode." Prior to being exposed or upon being exposed to disruptive energy field 11, IMD 14 is configured from a normal operating mode to the exposure operating mode. IMD 14 may be configured from the normal mode to the exposure mode automatically, e.g., in response to detection of disruptive energy field 11, or manually programmed into the exposure mode via an external programming device 18.

In the normal operating mode, IMD 14 operates in accordance with all desired functionality using settings programmed by a physician, clinician or other user. When operating in the normal operating mode, IMD 14 may perform functions in a manner that does not specifically account for the presence of strong disruptive energy fields. The normal mode may correspond with the operating mode that a physician or other user feels provides a most efficacious therapy for patient 12. While operating in accordance with the normal operating mode, IMD 14 may sense physiological events, deliver a number of different therapies, and log collected data.

In the exposure mode, however, IMD 14 may perform functions in a manner that specifically accounts for the presence of strong disruptive energy fields. While operating in the exposure mode, IMD 14 may be configured to operate with different functionality than when operating in the normal operating mode. IMD 14 may, in some instances, be configured to operate with reduced functionality. In other words, when configured to operate in the exposure mode, IMD 14 may have only a subset of the functionality of the normal operating mode. For example, IMD 14 may not provide sensing, not deliver therapy, delivery only a subset of possible therapies, not log collected data or the like. In other instances, IMD 14 may be operating with approximately the same functionality or even increased functionality in the exposure mode. For example, IMD 14 may use a different sensor or algorithm to detect cardiac activity of the heart of patient 12, such as pressure sensor measurements rather than electrical activity of the heart. In either case, it is desirable that IMD 14 be reconfigured from the exposure operating mode to the normal operating mode as soon as safely possible after exiting from environment 10.

In accordance with one aspect of this disclosure, IMD 14 may track an amount of time that has elapsed since configuring IMD 14 from the normal operating mode to the exposure operating mode and monitor for presence of disruptive energy field 11. IMD 14 may switch from the exposure operating mode back to the normal operating mode (or to a different operating mode) when (i) the amount of time that has elapsed since configuring IMD 14 from the normal operating mode to the exposure operating mode exceeds a threshold amount of time and (ii) the disruptive energy field is detected before the amount of time exceeds the threshold amount of time and the disruptive energy field is not currently detected. When either of these conditions is not met, IMD 14 continues to operate in accordance with the exposure mode.

By requiring that both of these conditions are met before disabling the exposure operating mode, IMD 14 may automatically reconfigure itself back to the normal operating mode without manual programming by a user while preventing the exposure operating mode from being disabled before patient 12 has actually undergone the MRI scan or is currently undergoing the MRI scan. As an added safety mechanism, IMD 14 may wait until IMD 14 has been out of environment 10 for a particular amount of time before automatically reconfiguring to the normal mode. In this manner, IMD 14 may allow for the system and/or the patient's physiology (e.g., capture thresholds, sensing amplitudes, and lead impedances) to stabilize after exposure to environment 10.

Although described with respect to a medical environment, the techniques of this disclosure may be used to operate IMD 14 within non-medical environments that include disruptive energy fields. Additionally, the techniques of this disclosure may also be used to operate IMD 14 within environments that produce disruptive energy fields that are intermittent in nature.

Figure 2:
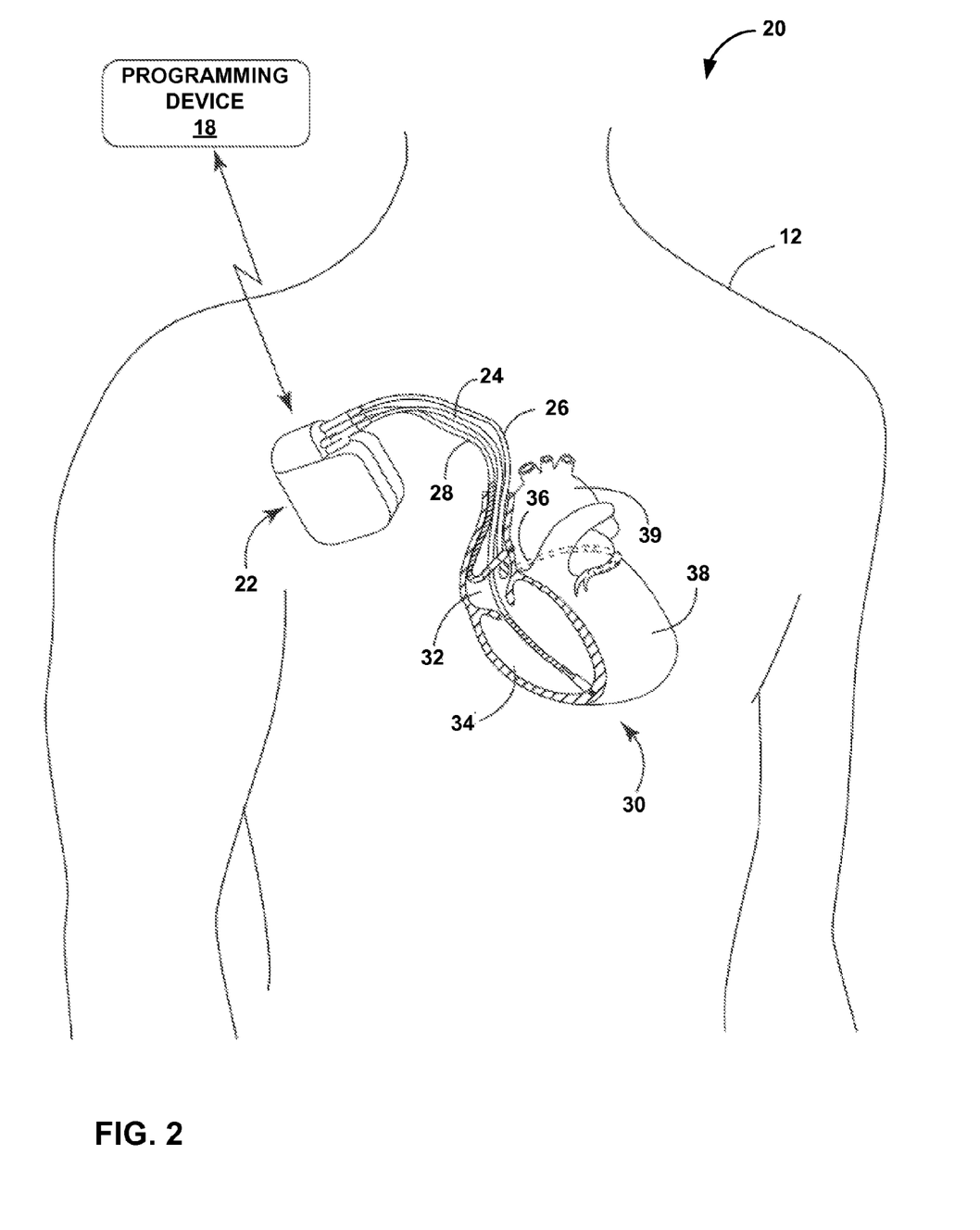
FIG. 2 is a conceptual diagram illustrating an example therapy system that may be used to provide therapy to patient.

FIG. 2 is a conceptual diagram illustrating an example therapy system 20 that may be used to provide therapy to patient 12. Therapy system 20 includes an IMD 22 and leads 24, 26 and 28 that extend from IMD 22. IMD 22 may, for example, correspond to IMD 14 of FIG. 1 or another IMD. Therapy system 20 may also include a programming device 18 that is wirelessly coupled to IMD 22.

In the example illustrated in FIG. 2, IMD 22 is an implantable cardiac device that provides electrical stimulation therapy to a heart 30 of patient 12. The electrical stimulation therapy to heart 30, sometimes referred to as cardiac rhythm management therapy, may include pacing, cardioversion, defibrillation and/or cardiac resynchronization therapy (CRT). In some examples, IMD 22 delivers pacing pulses, but not cardioversion or defibrillation shocks, while in other examples, IMD 22 delivers cardioversion or defibrillation shocks, but not pacing pulses. In addition, in further examples, IMD 22 delivers pacing pulses, cardioversion shocks, and defibrillation shocks. As such, IMD 22 may operate as an implantable pacemaker, cardioverter, and/or defibrillator.

IMD 22 may deliver the electrical stimulation therapy to heart 30 via electrodes (not shown in FIG. 2) coupled to leads that are implanted within or adjacent to one or more atria or ventricles of heart 30. In the example illustrated in FIG. 2, leads 24, 26 and 28 are coupled to IMD 22 and extend into heart 30 of patient 12. In the example shown in FIG. 2, right ventricular (RV) lead 24 extends through one or more veins (not shown), the superior vena cava (not shown), and right atrium 32, and into right ventricle 34 of heart 30. Left ventricular (LV) coronary sinus lead 26 extends through one or more veins, the vena cava, right atrium 32, and into the coronary sinus 36 to a region adjacent to the free wall of left ventricle 38 of heart 30. Right atrial (RA) lead 28 extends through one or more veins and the vena cava, and into the right atrium 32 of heart 30. In other examples, IMD 22 may deliver stimulation therapy to heart 14 by delivering stimulation to an extravascular tissue site in addition to or instead of delivering stimulation via electrodes of intravascular leads 24, 26 and 28.

In addition to delivering therapy to heart 30, electrodes of leads 24, 26 and 28 may sense electrical signals attendant to the depolarization and repolarization of heart 30 (e.g., cardiac signals). IMD 14 may analyze the sensed signals to monitor a rhythm of the heart or detect an arrhythmia of heart 30, e.g., tachycardia, bradycardia, fibrillation or the like. In some instances, IMD 22 provides pacing pulses to heart 30 based on the cardiac signals sensed within heart 30. IMD 22 may also provide defibrillation therapy and/or cardioversion therapy via electrodes located on at least one of the leads 24, 26 and 28. IMD 22 may detect arrhythmia of heart 30 based on the sensed cardiac signals and deliver defibrillation therapy to heart 30 in the form of electrical shocks. In some examples, IMD 22 may be programmed to deliver a progression of therapies, e.g., shocks with increasing energy levels, until the arrhythmia of heart 30 is stopped.

A user, such as a physician, technician, or other clinician, may interact with a programming device 18 to communicate with IMD 22. For example, the user may interact with programming device 18 to retrieve physiological or diagnostic information from IMD 22. For example, the user may use programming device 18 to retrieve information from IMD 22 regarding the rhythm of the heart of patient 12, trends therein over time, or cardiac arrhythmia episodes. As another example, the user may use programming device 18 to retrieve information from IMD 22 regarding other sensed physiological parameters of patient 12, such as electrical depolarization/repolarization signals from the heart (referred to as "electrogram" or EGM), intracardiac or intravascular pressure, activity, posture, respiration or thoracic impedance. As another example, the user may use programming device 18 to retrieve information from IMD 22 regarding the performance or integrity of IMD 22 or other components of therapy system 20, such as leads or a power source of IMD 22.

The user may also interact with programming device 18 to program IMD 22, e.g., select values for operational parameters of IMD 22. For electrical stimulation therapies, for example, the user may interact with programming device 18 to program a therapy progression, select an electrode or combination of electrodes of leads 24, 26 and 28 to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like. By programming these parameters, the physician or other user can attempt to generate an efficacious therapy for patient 12 that is delivered via the selected electrodes.

In some instances, a user interacts with programming device 18 to program IMD 22 into the exposure mode prior to patient 12 undergoing a medical procedure in which IMD 22 will be exposed to a disruptive energy field 11, e.g., before undergoing a MRI scan. The user may also reprogram IMD 22 from the exposure mode to a normal mode after the MRI scan is finished. Often times, an individual performing the MRI scan is not familiar with programming implanted devices. As such, a technician familiar with programming implanted devices needs to be present before and after the medical procedure, the MRI scan in this case. This is often burdensome as the medical procedure may take several hours.

As such, IMD 22 may automatically reconfigure itself into the normal operating mode in accordance with the techniques described in this disclosure. In other words, IMD 22 may revert to the normal operating mode without the technician using programming device 18 to manually reprogram IMD 22. For example, IMD 22 may track an amount of time that has elapsed since configuring IMD 22 into the exposure operating mode and monitor for presence of disruptive energy field 11. IMD 22 reverts from the exposure operating mode back to the normal operating mode (or to a different operating mode) when (i) the amount of time that has elapsed since configuring IMD 22 into the exposure operating mode exceeds a threshold amount of time and (ii) the disruptive energy field was detected before the amount of time exceeds the threshold amount of time and the disruptive energy field is not currently detected. The techniques of this disclosure may be used regardless of whether IMD 22 was configured into the exposure mode manually via programming device 18 or automatically in response to detecting disruptive energy field 11.

Programming device 18 may be a dedicated hardware device with dedicated software for programming of IMD 22. Alternatively, programming device 18 may be an off-the-shelf computing device running an application that enables programming device 18 to program IMD 22. In some examples, programming device 18 may be a handheld computing device or a computer workstation. Programming device 18 may, in some instances, include a programming head that may be placed proximate to the patient's body near the implant site of IMD 22 in order to improve the quality or security of communication between IMD 22 and programming device 18. Programming device 18 may include a user interface that receives input from the user and/or displays data to the user.

Programming device 18 may communicate with IMD 22 via wireless communication using any techniques known in the art. Examples of communication techniques may include, for example, magnetic telemetry, low frequency telemetry or radiofrequency (RF) telemetry, but other techniques are also contemplated. In some instances, programming device 18 and IMD 22 may communicate in the 402-405 MHz frequency band in accordance with the Medical Implant Communications Service (MICS) protocol.

Figure 3:
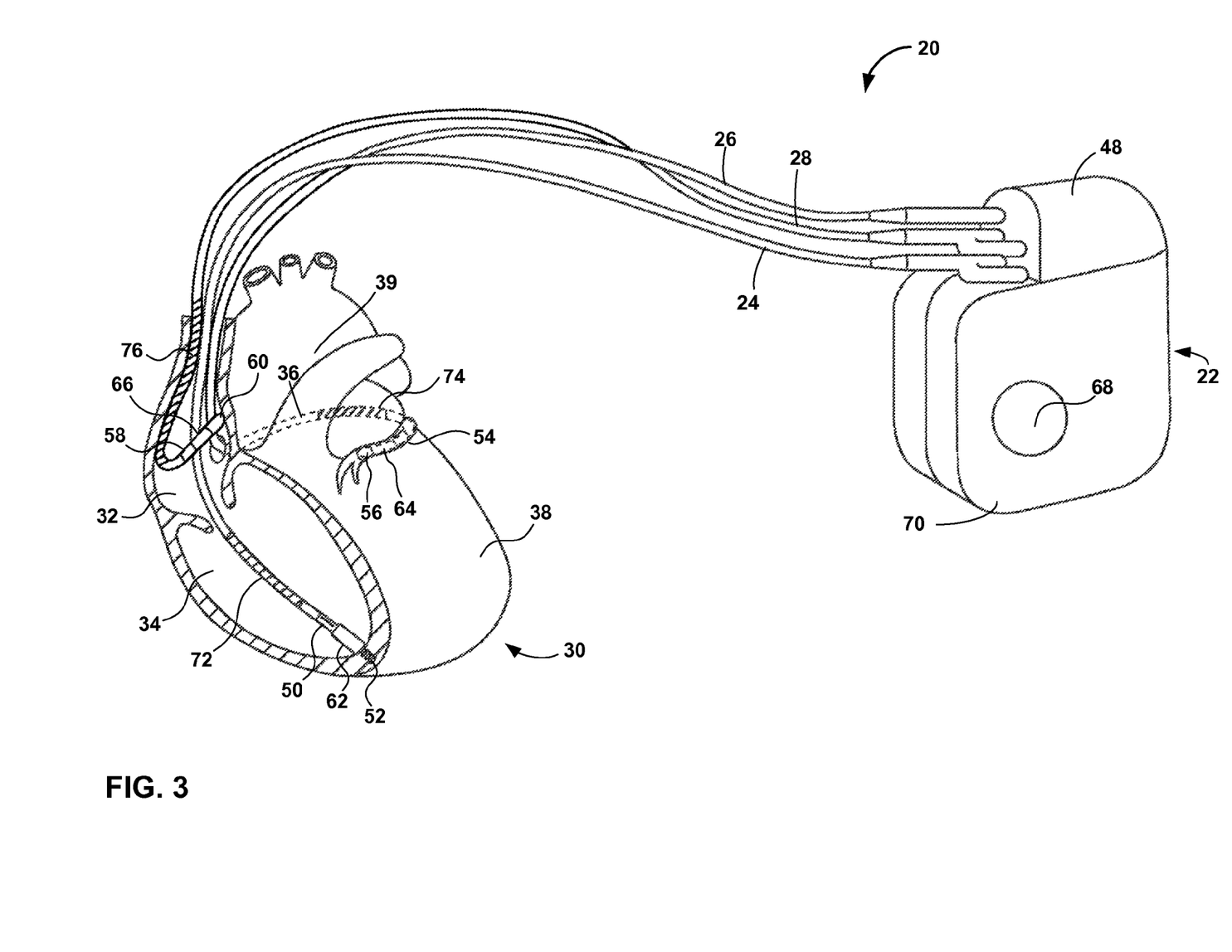
FIG. 3 is a conceptual diagram illustrating the implantable medical device and leads of the therapy system of FIG. 2 in greater detail.

FIG. 3 is a conceptual diagram illustrating IMD 22 and leads 24, 26 and 28 of therapy system 20 in greater detail. Leads 24, 26 and 28 may be electrically coupled to a stimulation module, a sensing module, or other modules of IMD 22 via connector block 48. In some examples, proximal ends of leads 24, 26 and 28 may include electrical contacts that electrically couple to respective electrical contacts within connector block 48. In addition, in some examples, leads 24, 26 and 28 may be mechanically coupled to connector block 48 with the aid of set screws, connection pins or another suitable mechanical coupling mechanism.

Each of the leads 24, 26 and 28 includes an elongated insulative lead body, which may carry a number of concentric coiled conductors separated from one another by tubular insulative sheaths. Other lead configurations are also contemplated, such as lead configurations that do not include coiled conductors, but instead a different type of conductor. In the illustrated example, bipolar electrodes 50 and 52 are located proximate to a distal end of lead 24. In addition, bipolar electrodes 54 and 56 are located proximate to a distal end of lead 26 and bipolar electrodes 58 and 60 are located proximate to a distal end of lead 28.

Electrodes 50, 54, and 58 may take the form of ring electrodes, and electrodes 52, 56, and 60 may take the form of extendable helix tip electrodes mounted retractably within insulative electrode heads 62, 64, and 66, respectively. Each of the electrodes 50, 52, 54, 56, 58, and 60 may be electrically coupled to a respective one of the conductors within the lead body of its associated lead 24, 26 and 28, and thereby coupled to respective ones of the electrical contacts on the proximal end of leads 24, 26 and 28. In other embodiments, electrodes 50, 52, 54, 56, 58, and 60 may be other types of electrodes.

Electrodes 50, 52, 54, 56, 58, and 60 may sense electrical signals attendant to the depolarization and repolarization of heart 30. The electrical signals are conducted to IMD 22 via the one or more conductors of respective leads 24, 26 and 28. In some examples, IMD 22 also delivers pacing pulses via electrodes 50, 52, 54, 56, 58, and 60 to cause depolarization of cardiac tissue of heart 14. In some examples, as illustrated in FIG. 3, IMD 22 includes one or more housing electrodes, such as housing electrode 68, which may be formed integrally with an outer surface of hermetically-sealed housing 70 of IMD 22 or otherwise coupled to housing 70. In some examples, housing electrode 68 is defined by an uninsulated portion of an outward facing portion of housing 70 of IMD 22. In some examples, housing electrode 68 comprises substantially all of housing 70. Divisions between insulated and uninsulated portions of housing 70 may be employed to define two or more housing electrodes. Any of the electrodes 50, 52, 54, 56, 58, and 60 may be used for unipolar sensing or pacing in combination with housing electrode 68. As such, the configurations of electrodes used by IMD 22 for sensing and pacing may be unipolar or bipolar depending on the application. As described in further detail with reference to FIG. 4, housing 70 may enclose a stimulation module that includes one or more signal generators that generate cardiac pacing pulses, resynchronization pulses defibrillation shocks or cardioversion shocks, as well as a sensing module for monitoring the patient's heart rhythm.

Leads 24, 26 and 28 also include elongated electrodes 72, 74, and 76, respectively, which may, in some instances, take the form of a coil. IMD 22 may deliver defibrillation pulses to heart 30 via any combination of elongated electrodes 72, 74, and 76, and housing electrode 68. Electrodes 68, 72, 74, and 76 may also be used to deliver cardioversion shocks to heart 30. Electrodes 50, 52, 54, 56, 58, 68, 72, 74, and 76 may be fabricated from any suitable electrically conductive material, including, but not limited to, platinum, platinum alloy or other materials known to be usable in implantable defibrillation electrodes.

As described above, exposure of IMD 22 to disruptive energy field 11 (FIG. 1) may result in undesirable operation. For example, gradient magnetic and RF fields produced by MRI scanner 16 (FIG. 1) may induce energy on one or more of electrodes 50, 52, 54, 56, 58, 72, 74, and 76 of respective ones of implantable leads 24, 26 and 28 or on electrode 68 of housing 70. In some instances, IMD 22 inappropriately detects the induced energy on electrodes 50, 52, 54, 56, 58, 68, 72, 74, and 76 as physiological signals, which may in turn cause IMD 22 to deliver undesired therapy or withhold desired therapy. In other instances, the induced energy on electrodes 50, 52, 54, 56, 58, 72, 74, and 76 result in IMD 22 not detecting physiological signals that are actually present, which may again result in IMD 22 delivering undesired therapy or withholding desired therapy. In further instances, the induced energy on electrodes 50, 52, 54, 56, 58, 72, 74, and 76 result in stimulation or heating of the tissue and/or nerve site adjacent to electrodes 50, 52, 54, 56, 58, 72, 74, and 76. Such heating may result in thermal damage to the tissue adjacent the electrodes, possibly compromising pacing and sensing thresholds at the site. Configuring IMD 22 into the exposure mode may reduce, and possibly eliminate, the undesirable operation of IMD 22.

The configuration of therapy system 20 illustrated in FIGS. 2 and 3 are merely examples. In other examples, therapy system 20 may include more or fewer leads extending from IMD 22. For example, IMD 22 may be coupled to two leads, e.g., one lead implanted within right atrium 32 and the other implanted within right ventricle 34. In another example, IMD 22 may be coupled to a single lead that is implanted within either an atrium or ventricle of heart 30. As a further example, the therapy system may include three transvenous leads located as illustrated in FIGS. 2 and 3, and an additional lead located within or proximate to left atrium 39. As such, IMD 22 may be used for single chamber or multi-chamber cardiac rhythm management therapy. In addition to more or fewer leads, each of leads 24, 26 and 28 may include more or fewer electrodes. In instances in which IMD 22 is used only for pacing, for example, leads 24, 26 and 28 may not included electrodes 72, 74 and 76.

In still other examples, a therapy system may include epicardial leads and/or patch electrodes instead of or in addition to the transvenous leads 24, 26 and 28 illustrated in FIGS. 2 and 3. Further, IMD 22 need not be implanted within patient 12. In examples in which IMD 22 is not implanted in patient 12, IMD 22 may deliver defibrillation pulses and other therapies to heart 30 via percutaneous leads that extend through the skin of patient 12 to a variety of positions within or outside of heart 30.

The techniques of this disclosure are described in the context of cardiac rhythm management therapy for purposes of illustration. The techniques of this disclosure, however, may be used to operate an IMD that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. Moreover, the techniques may be used to operate an IMD that provides other types of therapy, such as drug delivery or infusion therapies. As such, description of these techniques in the context of cardiac rhythm management therapy should not be limiting of the techniques as broadly described in this disclosure.

Figure 4:
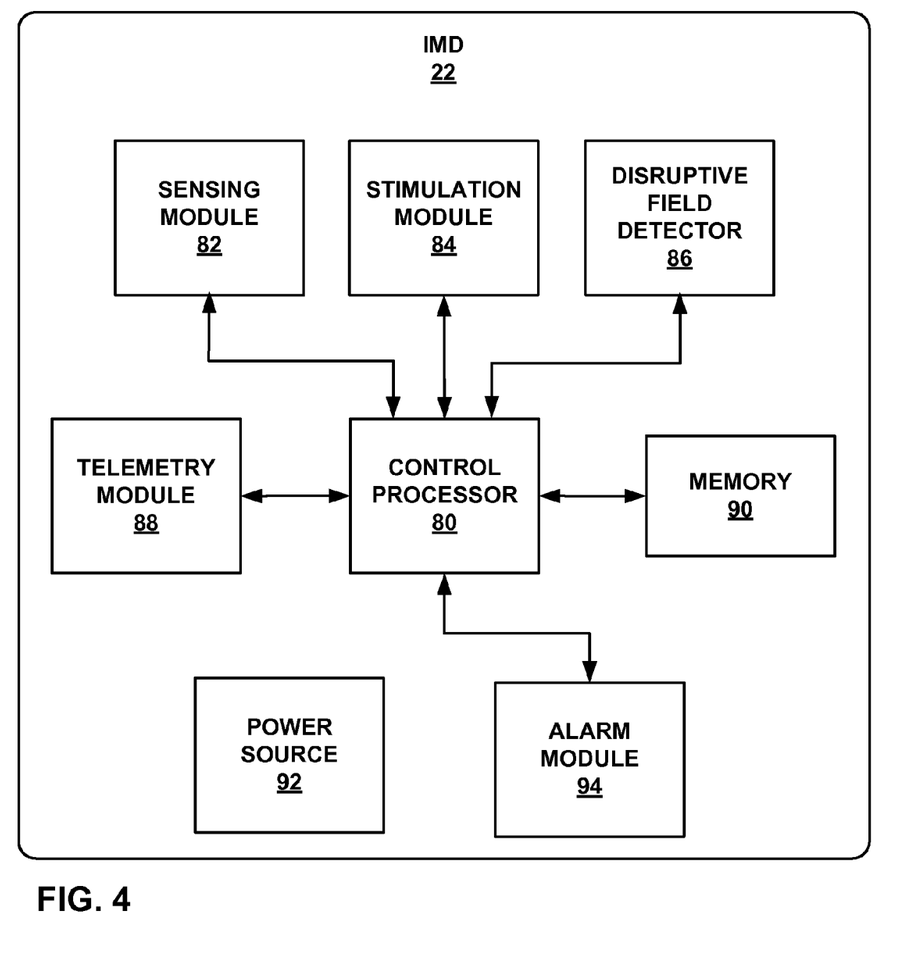
FIG. 4 is a functional block diagram of an example configuration of components of the implantable medical device of FIGS. 2 and 3.

FIG. 4 is a functional block diagram of an example configuration of components of IMD 22. In the example illustrated by FIG. 4, IMD 22 includes a control processor 80, sensing module 82, stimulation module 84, disruptive field detector 86, telemetry module 88, memory 90, power source 92 and alarm module 94. Memory 90 may include computer-readable instructions that, when executed by control processor 80, cause IMD 22 and/or processor 80 to perform various functions attributed to IMD 22 and processor 80 in this disclosure. Memory 90 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The various components of IMD 22 are coupled to power source 92, which may include a rechargeable or non-rechargeable battery. A non-rechargeable battery may be capable of holding a charge for several years, while a rechargeable battery may be inductively charged from an external device, e.g., on a daily or weekly basis. Power source 92 also may include power supply circuitry for providing regulated voltage and/or current levels to power the components of IMD 22.

Control processor 80 may include any one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, control processor 80 may include multiple components, such as any combination of one or more microprocessors, one or more controllers, one or more DSPs, one or more ASICs, or one or more FPGAs, as well as other discrete or integrated logic circuitry. The functions attributed to control processor 80 herein may be embodied as software, firmware, hardware or any combination thereof.

Control processor 80 controls stimulation module 84 to deliver electrical stimulation therapy to heart 30 via one or more of electrodes 50, 52, 54, 56, 58, 68, 72, 74 and 76 (FIG. 3). Stimulation module 84 is electrically coupled to electrodes 50, 52, 54, 56, 58, 68, 72, 74 and 76, e.g., via conductors of the respective lead 24, 26 and 28, or, in the case of housing electrode 68, via an electrical conductor disposed within housing 70 of IMD 22. Control processor 80 controls stimulation module 84 to deliver electrical pacing pulses or cardioversion or defibrillation shocks with the amplitudes, pulse widths, frequencies, electrode combinations or electrode polarities specified by a selected therapy program. For example, stimulation module 84 may deliver defibrillation shocks to heart 30 via at least two electrodes 68, 72, 74 and 76. As another example, electrical stimulation module 84 may deliver pacing pulses via ring electrodes 50, 54 and 58 coupled to leads 24, 26 and 28, respectively, and/or helical tip electrodes 52, 56 and 60 of leads 24, 26, and 28, respectively. Stimulation module 84 may deliver one or more of these types of stimulation in the form of other signals besides pulses or shocks, such as sine waves, square waves, or other substantially continuous signals.

Stimulation module 84 may include a switch module (not shown) and control processor 80 may use the switch module to select, e.g., via a data/address bus, which of the available electrodes are used to deliver pacing, resynchronization, cardioversion, or defibrillation pulses. The switch module may include a switch array, switch matrix, multiplexer, or any other type of switching device suitable to selectively couple stimulation energy to selected electrodes.

Sensing module 82 is configured to monitor signals from one or more sensors. In one example, sensing module 82 is configured to monitor signals sensed by one or more of electrodes 50, 52, 54, 56, 58, 68, 72, 74 and 76. In this manner, electrodes 50, 52, 54, 56, 58, 68, 72, 74 and 76 may operate as sense electrodes in addition to being used for delivering electrical stimulation therapy. In other instances, leads 24, 26 and 28 include one or more electrodes dedicated for sensing. In further examples, sensing module 82 is coupled to one or more sensors that are not included on leads 24, 26 and 28, e.g., via a wired or wireless coupling. Such sensors may include pressure sensors, accelerometers, flow sensors, blood chemistry sensors, activity sensors or other type of physiological sensor. Signals monitored by sensing module 82 may be stored in memory 90.

When sensing module 82 monitors signals sensed by one or more of electrodes 50, 52, 54, 56, 58, 68, 72, 74 and 76, electrode sensing configurations are defined by various combinations of the electrodes in order to monitor electrical activity of heart 30. Control processor 80 may select the electrodes that function as sense electrodes, sometimes referred to as a sensing configuration or sensing vector, in order to monitor electrical activity of heart 30. In one example, sensing module 82 may include a switch module (not shown) to select which of the available electrodes are used to sense the heart activity. Control processor 80 may select the electrodes that function as sense electrodes, or the sensing electrode configuration, via the switch module within sensing module 82, e.g., by providing signals via a data/address bus.

Sensing module 82 may include multiple detection channels, each of which may comprise an amplifier. The detection channels may be configured to detect different cardiac events, such as P-waves, R-waves, T waves, atrial pacing events, ventricular pacing events and the like. In response to the signals from control processor 80, the switch module within sensing module 82 may couple selected electrodes to each of the detection channels to acquire a desired EGM for detection of cardiac events, such as an electrocardiogram (ECG).

As described above, processor 80 may be configurable to operate IMD 22 in a number of different operating modes, such as the normal operating mode and the exposure operating mode. Although the techniques of this disclosure are described with respect to two modes, i.e., the normal and exposure mode, processor 80 may operate IMD 22 in accordance with and switch between more than two modes. In the normal operating mode, processor 80 operates IMD 22 in accordance with settings programmed by a physician, clinician or other user. The normal mode may correspond with the operating mode that a physician or other user feels provides a most efficacious therapy for patient 12. The normal operating mode may vary from patient to patient depending on the condition of patient 12 for which IMD 22 is providing therapy.

The normal operating mode of IMD 22 may be any of a number of pacing modes, including DDD, VVI, DVI, VDD, AAI, DDI, DDDR, VVIR, DVIR, VDDR, AAIR, DDIR, VOO, AOO, DOO, ODO and other modes of single and dual chamber pacing. For example, the normal operating mode may be an atrial based pacing mode, such as AAI or ADI pacing mode, if IMD 22 is providing therapy to a patient experiencing bradycardia. As another example, the normal operating mode may be a dual chamber pacing mode, such as a DDD pacing mode, if IMD 22 is providing therapy to a patient with unreliable A-V conduction.

In the aforementioned pacing modes, the abbreviations of which conform to the NBG Pacemaker Code, the first letter in the pacing mode indicates the chamber or chambers paced and may take on the letter "D" indicating dual chamber (i.e., atrial and ventricle both paced), "V" indicating a ventricle is paced, "A" indicating an atrium is paced, or "O" indicating no chamber is paced. The second letter indicates the chamber or chambers sensed and may take on the letter "D" indicating dual chamber (i.e., atrial and ventricle both paced), "V" indicating a ventricle is paced, "A" indicating an atrium is paced, or "O" indicating no chamber is paced. The third letter indicates mode or modes of response to sensing and may take on the letter "T" indicating triggered pacing (i.e., pacing is provided in response to the sensing), "I" indicating inhibited pacing (i.e., pacing is stopped based in response to the sensing), "D" indicating dual response (i.e., triggered and inhibited) and "O" for no response. The fourth letter indicates programmable functions and may take on the letter "R" indicating rate modulated pacing, as well as other letters not explained here. Although not described here, a fifth letter may be provided in accordance with the NBG Pacemaker Code indicating anti-tachycardia functions.

If IMD 22 is configured to generate and deliver pacing pulses to heart 30, control processor 80 may include a pacer timing and control module (not shown), which may be embodied as hardware, firmware, software, or any combination thereof. The pacer timing and control module may comprise a dedicated hardware circuit, such as an ASIC, separate from other components of control processor 80, such as a microprocessor, or a software module executed by a component of control processor 80, which may be a microprocessor or ASIC.

The pacer timing and control module may include programmable counters which control the basic time intervals associated with various single and dual chamber pacing modes. Intervals defined by the pacer timing and control module within control processor 80 may include, for example, atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals to sensing module 82 to blank one or more channels, e.g., amplifiers, for a period during and after delivery of electrical stimulation to heart 30. The durations of these intervals may be determined by control processor 80 in response to stored program data in memory 90. The pacer timing and control module of control processor 80 may also determine the amplitude of the cardiac pacing pulses.

During pacing, escape interval counters within the pacer timing and control module of control processor 80 may be reset upon sensing of R-waves and P-waves with detection channels of sensing module 82. Exposure of IMD 22 to disruptive energy field 11 or other noisy environment may produce oversensing of R-wave events that cause the ventricular escape interval counter to reset. The oversensed R-waves produced by one or more of the detection channels produce short R-R intervals that may inhibit delivery of pacing pulses.

Stimulation module 84 may include pacer output circuits that are coupled, e.g., selectively by a switching module, to any combination of electrodes 50, 52, 54, 56, 58, 68, 72, 74 and 76 appropriate for delivery of a bipolar or unipolar pacing pulse to one of the chambers of heart 30. Control processor 80 may reset the escape interval counters upon the generation of pacing pulses by stimulation module 84, and thereby control the basic timing of cardiac pacing functions, including anti-tachyarrhythmia pacing.

The value of the count present in the escape interval counters when reset by sensed R-waves and P-waves may be used by control processor 80 to detect cardiac events and measure the durations of R-R intervals, P-P intervals, P-R intervals and R-P intervals, which are measurements that may be stored in memory 90. Control processor 80 may use the count in the interval counters to detect a tachyarrhythmia event, such as an atrial or ventricular fibrillation or tachycardia. The R-R intervals indicated by the count, in particular, may be used to increment a VF counter to control delivery of cardioversion or defibrillation shocks. The VF counter may form part of a cardioversion/defibrillation control module (not shown) implemented by control processor 80. Again, the VF counter may be incremented in response to detection of short R-R intervals, and possibly in response to other events such as R-R interval variance. The VF counter triggers delivery of a defibrillation shock when the counter reaches a number of intervals for detection (NID) threshold.

In the event that control processor 80 detects an atrial or ventricular tachyarrhythmia based on signals from sensing module 82, and an anti-tachyarrhythmia pacing regimen is desired, timing intervals for controlling the generation of anti-tachyarrhythmia pacing therapies by stimulation module 84 may be loaded by control processor 80 into the pacer timing and control module to control the operation of the escape interval counters therein and to define refractory periods during which detection of R-waves and P-waves is ineffective to restart the escape interval counters.

Stimulation module 84 may also includes a high voltage charge circuit and a high voltage output circuit. In the event that generation of a cardioversion or defibrillation pulse is required, control processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, control processor 80 may activate the cardioversion/defibrillation control module, which may, like the pacer timing and control module, be a hardware component of control processor 80 and/or a firmware or software module executed by one or more hardware components of control processor 80. The cardioversion/defibrillation control module may initiate charging of the high voltage capacitors of the high voltage charge circuit of stimulation module 84 under control of a high voltage charging control line.

Control processor 80 may monitor the voltage on the high voltage capacitor, e.g., via a voltage charging and potential (VCAP) line. In response to the voltage on the high voltage capacitor reaching a predetermined value set by control processor 80, control processor 80 may generate a logic signal that terminates charging. Thereafter, timing of the delivery of the defibrillation or cardioversion shock by stimulation module 84 is controlled by the cardioversion/defibrillation control module of control processor 80. Following delivery of the fibrillation or tachycardia therapy, control processor 80 may return stimulation module 84 to a cardiac pacing function and await the next successive interrupt due to pacing or the occurrence of a sensed atrial depolarization (P-wave) or ventricular depolarization (R-wave).

When operating in the normal operating modes, processor 80 may initiate and/or adjust delivery of pacing pulses and/or defibrillation or cardioversion shocks based in part upon sensed physiological events. For instance, IMD 22 may withhold therapy in response to a sensed physiological event in pacing modes with inhibit ("I") response to sensing, deliver therapy in response to the sensed event in modes with triggered ("T") response to sensing or both in the case of dual inhibit and trigger ("D") response to sensing. These normal operating modes may therefore be susceptible to undesirable operation when IMD 22 is placed within environment 10 with disruptive energy field 11 as described in more detail below.

Disruptive energy field 11, which may, for example, comprise gradient magnetic fields and/or RF fields produced by MRI scanner 16 (FIG. 1), may induce energy on one or more electrodes of implantable leads 24, 26 and 28 coupled to IMD 22. In some instances, sensing module 82 inappropriately detects the induced energy on the leads as physiological signals, which may in turn cause undesirable operation of IMD 22. In other words, IMD 22 senses a physiological signal when one is not actually present.

When operating in a normal mode with inhibit response to sensing, processor 80 may not deliver (i.e., withhold) a desired pacing pulse in response to sensing the induced energy from the disruptive energy field as a physiological signal. For example, processor 80 may identify the induced energy as an R-wave event, thus producing short R-R intervals that may inhibit delivery of pacing pulses. In other instances when operating in a normal mode with dual inhibit and trigger response to sensing, processor 80 may also deliver an undesirable pacing pulse in addition to withholding a desired pacing pulse in response to sensing the induced energy from disruptive energy field 11 as a physiological signal. In particular, sensing the induced energy from the disruptive energy field as a physiological signal may inappropriately start an escape interval after which an undesired pacing pulse is delivered. This may result in dangerously fast heart rhythms and may lead to tachyarrhythmia or fibrillation.

In other instances, the induced energy on the leads result in IMD 22 not sensing actual physiological signals that are present. Processor 80 may, for example, initiate a blanking period in response to the induced energy on the leads. During the blanking period, sensing module 82 may power down one or more sense amplifiers. As such, sensing module 82 will fail to detect any actual (true) physiological event that occurs during the blanking period. Failure to detect this actual physiological event may again result in IMD 22 delivering undesired therapy or withholding desired therapy.

In further instances, the induced energy on one or more of leads 24, 26 and 28 may result in stimulation or heating of the tissue and/or nerve site adjacent to any of electrodes 50, 52, 54, 56, 58, 72, 74 and 76 of respective leads 24, 26 and 28. Such heating may result in thermal damage to the tissue adjacent the electrodes. For example, heating of tissue adjacent to atrial electrode 60 may result in damage to heart tissue in right atrium 32. This may in turn possibly compromise pacing and sensing thresholds at the site. Alternatively, or additionally, the damage to the tissue adjacent to the electrodes may result in a blocked A-V conduction.

To reduce the effects of disruptive energy field 11, processor 80 may be configured to operate IMD 22 in the exposure operating mode. The exposure operating mode is typically less susceptible to undesirable operation in disruptive energy field 11 than the normal operating mode. In other words, operating IMD 22 in the exposure mode may reduce if not eliminate the adverse effects that disruptive energy field 11 have on therapy delivery to patient 12. When operating in the exposure operating mode, processor 80 provides therapy with limited functionality compared to the normal operating mode. In other words, IMD 22 may have only a subset of the functionality compared to when operating in the normal operating mode.

To reduce the susceptibility to undesirable operation of IMD 22 due to sensing the induced energy on the leads as a physiological signal, processor 80 may operate IMD 22 in an exposure operating mode. In the exposure operating mode, processor 80 may control IMD 22 in a manner in which the induced energy on the leads does not affect delivery of therapy. For example, the exposure mode may correspond with a pacing mode that does not provide sensing functionality. If patient 12 is pacing dependent, for example, the exposure mode of IMD 22 may correspond to an asynchronous pacing mode with no sensing, e.g., AOO, VOO or DOO. In another example, the exposure mode of IMD 22 may correspond to an asynchronous pacing mode that includes sensing, but has no mode of response to the pacing, e.g., such as a AAO, AVO, ADO, VVO, VAO, VDO, DDO, DAO or DVO pacing mode. In either of these cases, pacing is provided with no modification due to sensing. As such, the induced energy on the leads caused by disruptive energy field 11 does not result in undesirable operation of IMD 22.

In a further example, the exposure mode of IMD 22 may correspond to a sensing only mode, such as OAO, OVO or ODO, in which no pacing is provided. Such modes may only be used in cases in which patient 12 is not pacing dependent. Because there is no pacing in these pacing modes, such pacing modes may prevent IMD 22 from delivering undesirable stimulation or withholding desirable stimulation. Thus, when operating in the exposure operating mode, IMD 22 may provide no stimulation or sensing, provide stimulation but no sensing or provide sensing but no stimulation.

The exposure mode may also suspend temporary operation of other functionality of IMD 22, particularly those that may function incorrectly when exposed to disruptive energy field 11. Some example functionality that may be suspended while operating in the exposure mode include tachycardia detection and therapy, fibrillation detection and therapy, impedance measurements, battery measurements, P- and R-wave measurements. Additional functionality that may be suspended while in the exposure mode includes collection of diagnostic data.

Processor 80 may be configured to operate IMD 22 in the exposure mode at some time prior to being exposed or immediately upon being exposed to disruptive energy field 11. For example, a user, such as a physician, clinician or technician, may manually program processor 80 to operate IMD 22 in the exposure mode using programming device 18. Under the control of processor 80, telemetry module 88 may receive downlink telemetry from and send uplink telemetry to programming device 18 with the aid of an antenna, which may be internal and/or external to IMD 22. Telemetry module 88 includes any suitable hardware, firmware, software or any combination thereof for communicating with another device, such as programming device 18. For example, telemetry module 88 may include appropriate modulation, demodulation, frequency conversion, filtering, and amplifier components for transmission and reception of data.

Alternatively, processor 80 may be configured to operate IMD 22 in the exposure mode automatically, e.g., in response to detection of disruptive energy field 11. IMD 22 may include one or more sensors, such as a disruptive field detector 86, that detect presence of disruptive energy field 11. Disruptive field detector 86 may include a magnetic field detector, such as a Hall sensor or a reed switch. In some instances, disruptive field detector 86 may be within housing 70 of IMD 22. For example, disruptive field detector 86 may be the same field detector used to sense a magnetic programming head of a programming device. Alternatively, IMD 22 may be coupled to a disruptive field detector 86 located outside of housing 70 of IMD 22.

Control processor 80 may receive one or more signals from disruptive field detector 86. The signal produced by disruptive field detector 86 may, for example, identify patient 12 has entered an environment in which IMD 22 is exposed to an energy field, e.g., a magnetic field, that is greater than or equal to a threshold level indicative of a disruptive energy field 11. In one example, processor 80 may utilize all or a subset of the detection methods described in U.S. Pat. No. 6,937,906 to Terry et al., entitled, "METHOD AND APPARATUS FOR DETECTING STATIC MAGNETIC FIELDS," which issued on Aug. 30, 2005 and which is incorporated herein by reference in its entirety. However, other disruptive field detection methodologies may also be employed by processor 80 in other examples to detect the presence of disruptive energy field 11.

Regardless of whether processor 80 of IMD 22 was manually configured using programming device 18 or automatically configured in response to detecting a disruptive energy field, it is desirable that processor 80 be reconfigured from the exposure operating mode to the normal operating mode as soon as safely possible after exiting from environment 10, e.g., due to the reduced or otherwise different functionality of the exposure mode. The techniques of this disclosure may be used to automatically revert processor 80 back to the normal operating mode when particular criteria that are indicative of the MRI being complete occur.

Processor 80 initiates a timing mechanism upon entering the exposure mode. Processor 80 uses the timing mechanism to track an amount of time that has elapsed since configuring processor 80 from the normal operating mode to the exposure operating mode. The timing mechanism may be a timer or other time-out mechanism that is capable of tracking an elapsed amount of time. The timer may be set to a predetermined time interval, such as an approximate length of the medical procedure and, in some instances, includes additional time for preexamination procedures and/or wait periods. In the case of a MRI scan, for example, the timer may be set to approximately one hour.

At the expiration of the timer, processor 80 determines whether IMD 22 has been exposed to disruptive energy field 11. In the case in which processor 80 is automatically configured into the exposure operating mode, IMD 22 will have been exposed to disruptive energy field 11 as this exposure is what triggered processor 80 to configure into the exposure mode. In the case of manual configuration using programming device 18, processor 80 may determine whether disruptive field detector 86 has detected exposure to disruptive energy field 11. For example, processor 80 may include a flip-flop and flip a bit of the flip-flop to indicate that the disruptive energy field 11 was detected.

If disruptive field detector 86 has not detected exposure to disruptive energy field 11, processor 80 may not revert back to operating IMD 22 in the normal operating mode. This is because the patient may not have had the MRI scan yet due to a longer than expected wait, technical problems or other issues that have delayed and/or cancelled the scheduled MRI scan. Reverting operation of IMD 22 back to the normal operating mode before the MRI scan may result in the undesirable operation described above. As such, processor 80 may require that disruptive field detector 86 detect the presence of disruptive energy field 11 prior to reverting back to the normal operating mode. Additionally, processor 80 requires that disruptive field detector 86 is not currently detecting the presence of disruptive energy field 11, i.e., IMD 22 is not currently being exposed to disruptive energy field 11, before reverting back to the normal operating mode. In this case, patient 12 may still be receiving the MRI scan.

Processor 80 may therefore continue to operate IMD 22 in the exposure mode when either no disruptive energy field is detected before the amount of time that has elapsed since configuring the IMD 22 into the exposure operating mode exceeds the threshold amount of time or the disruptive energy field is currently detected. In some instances, processor 80 may reset the timing mechanism if either of these conditions is met.

Processor 80 may automatically configure IMD 22 from the exposure operating mode back to the normal operating mode, i.e., disable the exposure mode, when (i) the amount of time that has elapsed since configuring IMD 22 from the normal operating mode to the exposure operating mode exceeds a threshold amount of time and (ii) the disruptive energy field was detected before the amount of time exceeds the threshold amount of time and the disruptive energy field is not currently detected. By requiring that both of these conditions are met before disabling the exposure operating mode, IMD 14 may automatically reconfigure itself back to the normal operating mode without manual programming by a user while preventing the exposure operating mode from being disabled before patient 12 has actually undergone the MRI scan or is currently undergoing the MRI scan.

In some instances, processor 80 may wait for a particular amount of time after the disruptive energy field is last detected before returning to the normal operating mode. For example, processor 80 may track an amount of time since the disruptive energy field was last detected and continue to operate IMD 22 in accordance with the exposure operating mode even when conditions (i) and (ii) are met when the amount of time since the disruptive energy field was last detected is less than a second threshold amount of time, e.g., five to ten minutes. Processor 80 may automatically configure IMD 22 from the exposure operating mode to the normal operating mode when the amount of time since the disruptive energy field was last detected is greater than or equal to the second threshold amount of time. This may serve as an extra precautionary measure to ensure that patient 12 has actually exited environment 10 permanently and not just entered briefly and then temporarily left, e.g., to take a phone call, use the restroom or other reason. Moreover, the additional time allows for therapy system 20 and/or the patient's physiology (e.g., capture thresholds, sensing amplitudes, and lead impedances) to stabilize after exposure to environment 10.

There may be times in which a patient's MRI scan may have been cancelled, rescheduled or otherwise delayed for an extended period of time. In such a case, disruptive field detector 86 will not detect the presence of disruptive energy field 11. As such, processor 80 will not automatically reconfigure from the exposure mode to the normal operating mode. As described above, however, it is desirable to revert back to the normal operating mode as soon as safely possible. To this end, processor 80 may reconfigure from the exposure mode to the normal mode after an extended period of time even though no disruptive energy field is detected. For example, processor 80 may reconfigure from the exposure mode to the normal mode after the timer has been reset and expired X times, where X is an integer greater than or equal to one. In another example, processor 80 may maintain a second timing mechanism, e.g., an extended timer, that is set equal to a period of time at which processor 80 will revert back to the normal operating mode regardless of whether disruptive energy field has been detected.

Upon reverting back to the normal operating mode when no disruptive energy field is detected, processor 80 may control alarm module 94 to provide an alert to patient 12 and/or a physician, clinician or technician that the device has reverted back to the normal operating mode without detecting a disruptive energy field. Alarm module 94 may include alarm circuitry to provide an audible alert, a perceptible muscle vibration, muscle stimulation or other sensory stimulation to notify the patient that an alert condition has been detected, e.g., reversion to the normal operating mode without detection of the disruptive energy field. Additionally, or alternatively, processor 80 may cause telemetry module 88 to transmit an alert or other signal, e.g., to programming device 18, to notify a physician, clinician or technician of the reversion to the normal operating mode. In this manner, the telemetry signal may function as the alert mechanism.

In another example, processor 80 may not automatically revert back to the normal operating mode without detecting the disruptive energy field. Instead, processor 80 may control alarm module 94 to provide an alert to indicate that the implantable medical device has been operating in the exposure mode for longer than a maximum desired period of time. In this case, the alert may prompt patient 12 to visit a physician, clinician or technician to have processor 80 reconfigured back to the normal operating mode.

While operating in the exposure operating mode, processor 80 may collect information that could be useful in future medical decisions and/or therapy programming. For example, processor 80 may track the duration of time IMD 22 was exposed to the disruptive energy field, the duration of time between enabling the exposure mode and exposure to the disruptive energy field, and the duration of time between exposure to disruptive energy field 11 and the disabling of the exposure mode (i.e., the reconfiguration to the normal operating mode). To do so, processor 80 may store a time and date stamp in memory 92 at times in which particular events occur.

For example, processor 80 may store a time and date stamp upon being configured into the exposure mode, upon disruptive field detector 86 detecting disruptive energy field 11, upon disruptive field detector 86 detecting the absence of disruptive energy field 11, upon processor 80 being reconfigured to the normal operating mode and the like. Processor 80 may, process these time and date stamps to compute the information and/or provide the time and date stamps to a programming device that may use them to compute the desired information. This information regarding the configuration and exposure may be used to improve clinical workflows, set threshold timer values, determine cumulative exposures and the like.

Figure 5:
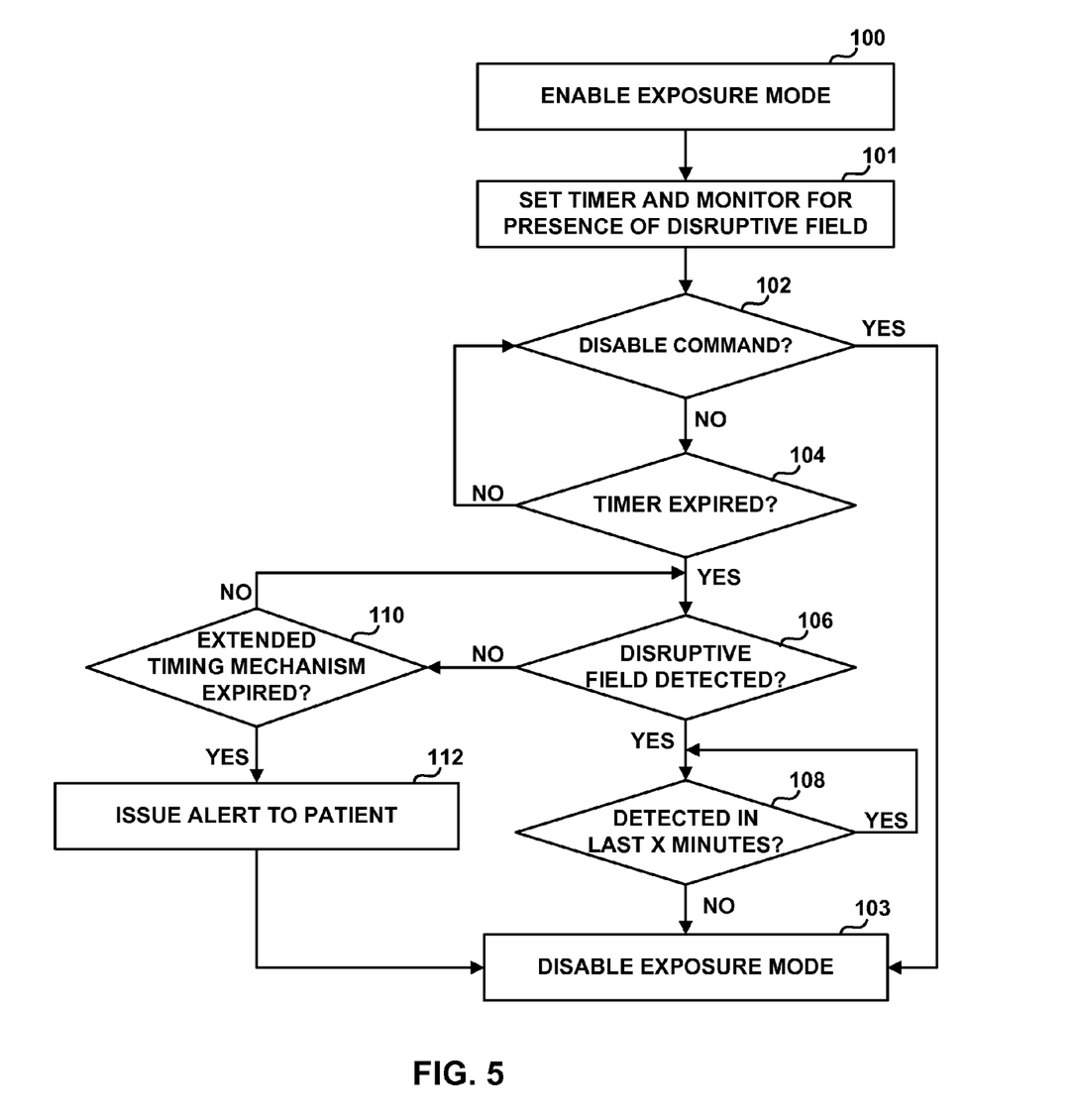
FIG. 5 is a flow diagram illustrating example operation of an implantable medical device automatically disabling the exposure mode in accordance with techniques of this disclosure.

FIG. 5 is a flow diagram illustrating example operation of IMD 22 in accordance with techniques of this disclosure. Initially, processor 80 enables the exposure operating mode at some time prior to being exposed or immediately upon being exposed to disruptive energy field 11 (100). Processor 80 may be programmed to enable the exposure mode manually, e.g., using programming device 18, or automatically, e.g., in response to detection of disruptive energy field 11. Processor 80 sets a timer and monitors for the presence of disruptive energy field 11 (101). Processor 80 uses the timer to track an amount of time that has elapsed since enabling the exposure mode, i.e., configuring processor 80 from the normal operating mode to the exposure operating mode. The timer may be set to a predetermined time interval, such as an approximate length of the medical procedure and, in some instances, includes additional time for preexamination procedures and/or wait periods.

As described above, it is desirable that processor 80 be reconfigured from the exposure operating mode to the normal operating mode as soon as safely possible after exiting from environment 10. Processor 80 determines whether a disable command has been received from programming device 18 (102). When a disable command is received ("YES" branch of 102), processor 80 disables the exposure mode and returns operation of IMD 22 to the normal operating mode (103). In this case, processor 80 of IMD 22 is manually reconfigured back to the normal operating mode.

When no disable command is received ("NO" branch of 102), processor 80 determines whether the timer has expired (104). When the timer has not expired ("NO" branch of 104), processor 80 again determines whether a disable command to manually disable the exposure mode has been received. When the timer has expired ("YES" branch of 104), processor 80 determines whether disruptive energy field 11 has been detected (106). When processor 80 determines that disruptive energy field 11 has been detected, processor 80 may optionally determine whether disruptive energy field 11 has been detected within the last X minutes (108). When disruptive energy field 11 has not been detected within the last X minutes, processor 80 disables the exposure mode (103). In some instances, processor 80 may control alarm module 94 to provide an alert to patient 12 notifying patient 12 that IMD 22 has reverted back to the normal operating mode. When disruptive energy field 11 has been detected within the last X minutes, processor 80 continues to wait until the disruptive energy field 11 has not been detected for the last X minutes. X may take on any integer or non-integer value greater than or equal to zero. Block 108 is an optional step in the process described in FIG. 5, in which case X may be equal to zero.

If no disruptive energy field has been detected ("NO" branch of 106), processor 80 may determine whether an extended timing mechanism has expired (110). The extended timing mechanism, which may be separate from the timer, is set equal to a period of time at which processor 80 will revert back to the normal operating mode regardless of whether disruptive energy field has been detected. In some instances, processor 80 may reset the timer a particular number of times instead of maintaining a separate timing mechanism. When the extended timing mechanism has not expired ("NO" branch of 110), processor 80 continues to monitor for detection of the disruptive energy field.

When the extended timing mechanism has not expired ("YES" branch of 110), processor 80 may control alarm module 94 to provide an alert to patient 12 notifying patient 12 that IMD 22 has reverted back to the normal operating mode without detecting a disruptive energy field (112). Processor 80 may then disable the exposure mode (103). In another example, processor 80 may not automatically revert back to the normal operating mode without detecting the disruptive energy field. Instead, processor 80 may control alarm module 94 to provide an alert to indicate that the implantable medical device has been operating in the exposure mode for longer than a maximum desired period of time. In this case, the alert may prompt patient 12 to visit a physician, clinician or technician to have processor 80 reconfigured back to the normal operating mode.

While the preceding description has been described primarily with reference to a therapy system including an IMD that delivers cardiac rhythm management therapy, e.g., IMD 22, the techniques described herein may be applicable to other therapy systems. For example, the techniques described herein may be applicable to systems including an IMD that delivers electrical stimulation therapy to other muscles, nerves or organs of patient 12. As another example, the techniques described herein may be applicable to systems including an implantable drug delivery or infusion device or an IMD including a drug delivery or infusion module. Other combinations of implantable devices will be obvious to one of skill in the art, and fall within the scope of this disclosure.

The techniques described in this disclosure, including those attributed to IMD 22, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
configuring an implantable medical device from a first operating mode to a second operating mode that is less susceptible to undesirable operation in a disruptive energy field than the first operating mode;

setting a timing mechanism to track an amount of time that has elapsed since configuring the implantable medical device from the first operating mode to the second operating mode;

monitoring for presence of the disruptive energy field;

automatically configuring the implantable medical device from the second operating mode to the first operating mode when (i) the amount of time that has elapsed since configuring the implantable medical device from the first operating mode to the second operating mode exceeds a threshold amount of time and (ii) the disruptive energy field was detected before the amount of time exceeds the threshold amount of time and the disruptive energy field is not currently detected; and continuing to operate the implantable medical device in accordance with the second operating mode when condition (i) is met and no disruptive energy field is detected between when the implantable medical device is configured from the first operating mode to the second operating mode and when condition (i) is met.

2. The method of claim 1, further comprising continuing to operate the implantable medical device in accordance with the second operating mode when the disruptive energy field is currently detected.

3. The method of claim 1, wherein the threshold amount of time is a first threshold amount of time, the method further comprising:

tracking an amount of time since the disruptive energy field was last detected;

continuing to operate the implantable medical device in accordance with the second operating mode even when conditions (i) and (ii) are met when the amount of time since the disruptive energy field was last detected is less than a second threshold amount of time; and configuring the implantable medical device from the second operating mode to the first operating mode when the amount of time since the disruptive energy field was last detected is greater than or equal to the second threshold amount of time.

4. The method of claim 1, further comprising resetting the timing mechanism when no disruptive energy field is detected before the amount of time that has elapsed since configuring the implantable medical device to the second operating mode exceeds the threshold amount of time.

5. The method of claim 1, wherein configuring the implantable medical device from the first operating mode to the second operating mode comprises configuring the implantable medical device in response to one of receiving a communication from a programming device or detecting the disruptive energy field.

6. The method of claim 1, further comprising:

switching from the second operating mode to the first operating mode when the implantable medical device has been operating in the second operating mode for more than a second threshold time period; and providing an alarm to indicate the switching from the second operating mode to the first operating mode.

7. The method of claim 1, further comprising providing an alert to indicate that the implantable medical device has been operating in the exposure mode for longer than a threshold period of time.

8. The method of claim 1, wherein the second operating mode comprises one of the implantable medical device providing no stimulation or sensing, the implantable medical device providing stimulation but no sensing, or the implantable medical device providing sensing but no stimulation.

9. The method of claim 1, wherein the disruptive energy field comprises one of a magnetic field, an electric field and an electromagnetic field.

10. An implantable medical device comprising:

means for configuring the implantable medical device from a first operating mode to a second operating mode that is less susceptible to undesirable operation in a disruptive energy field than the first operating mode;

means for tracking an amount of time that has elapsed since configuring the implantable medical device from the first operating mode to the second operating mode; and means for monitoring for presence of the disruptive energy field;

wherein the configuring means automatically configures the implantable medical device from the second operating mode to the first operating mode when (i) the amount of time that has elapsed since configuring the implantable medical device from the first operating mode to the second operating mode exceeds a threshold amount of time and (ii) the disruptive energy field was detected before the amount of time exceeds the threshold amount of time and the disruptive energy field is not currently detected, and wherein the device continues to operate in accordance with the second operating mode when condition (i) is met and no disruptive energy field is detected between when the implantable medical device is configured from the first operating mode to the second operating mode and when condition (i) is met.

11. The device of claim 10, wherein the device continues to operate in accordance with the second operating mode when the disruptive energy field is currently detected.

12. The device of claim 10, wherein the threshold amount of time is a first threshold amount of time, the device further comprising means for tracking an amount of time since the disruptive energy field was last detected, wherein the device continues to operate in accordance with the second operating mode even when conditions (i) and (ii) are met when the amount of time since the disruptive energy field was last detected is less than a second threshold amount of time; and the configuring means configures the device from the second operating mode to the first operating mode when the amount of time since the disruptive energy field was last detected is greater than or equal to the second threshold amount of time.

13. The device of claim 10, further comprising means for resetting the timing mechanism when no disruptive energy field is detected before the amount of time that has elapsed since configuring the implantable medical device to the second operating mode exceeds the threshold amount of time.

14. The device of claim 10, wherein the configuring means configured the device from the first operating mode to the second operating mode in response to one of receiving a communication from a programming device or detecting the disruptive energy field.

15. The device of claim 10, further comprising:

means for switching from the second operating mode to the first operating mode when the implantable medical device has been operating in the second operating mode for more than a second threshold time period; and means for providing an alarm to indicate the switching from the second operating mode to the first operating mode.

16. The device of claim 10, further comprising means for providing an alert to indicate that the implantable medical device has been operating in the exposure mode for longer than a threshold period of time.

17. The device of claim 10, wherein the second operating mode comprises one of the implantable medical device providing no stimulation or sensing, the implantable medical device providing stimulation but no sensing, or the implantable medical device providing sensing but no stimulation.

18. The device of claim 10, wherein the disruptive energy field comprises one of a magnetic field, an electric field and an electromagnetic field.

19. An implantable medical device comprising:
a processor programmed to configure the implantable medical device from a first operating mode to a second operating mode that is less susceptible to undesirable operation in a disruptive energy field than the first operating mode;
a timing mechanism to track an amount of time that has elapsed since configuring the implantable medical device from the first operating mode to the second operating mode; and
a disruptive field detector to monitor for presence of the disruptive energy field;
wherein the processor is programmed to automatically configure the implantable medical device from the second operating mode to the first operating mode when (i) the amount of time that has elapsed since configuring the implantable medical device from the first operating mode to the second operating mode exceeds a threshold amount of time and (ii) the disruptive energy field was detected before the amount of time exceeds the threshold amount of time and the disruptive energy field is not currently detected, and
wherein the processor is programmed to continue to operate the implantable medical device in accordance with the second operating mode when condition (i) is met and no disruptive energy field is detected between when the implantable medical device is configured from the first operating mode to the second operating mode and when condition (i) is met.

20. The device of claim 19, wherein the processor is programmed to continue to operate the implantable medical device in accordance with the second operating mode when the disruptive energy field is currently detected.

21. The device of claim 19, wherein the threshold amount of time is a first threshold amount of time, the device further comprising a second timing mechanism to track an amount of time since the disruptive energy field was last detected, wherein:
the processor is programmed to continue to operate the implantable medical device in accordance with the second operating mode even when conditions (i) and (ii) are met when the amount of time since the disruptive energy field was last detected is less than a second threshold amount of time; and
the processor is programmed to configure the implantable medical device from the second operating mode to the first operating mode when the amount of time since the disruptive energy field was last detected is greater than or equal to the second threshold amount of time.

22. The device of claim 19, wherein the processor is programmed to reset the timing mechanism when no disruptive energy field is detected before the amount of time that has elapsed since configuring the implantable medical device to the second operating mode exceeds the threshold amount of time.

23. The device of claim 19, wherein the processor is programmed to configure the implantable medical device from the first operating mode to the second operating mode in response to one of receiving a communication from a programming device or detecting the disruptive energy field.

24. The device of claim 19, wherein the processor is programmed to switch from the second operating mode to the first operating mode when the implantable medical device has been operating in the second operating mode for more than a second threshold time period, the device further comprising:
an alarm module to provide an alert indicating the switching from the second operating mode to the first operating mode.

25. The device of claim 19, further comprising an alarm module to provide an alert to indicate that the implantable medical device has been operating in the exposure mode for longer than a threshold period of time.

26. The device of claim 19, wherein the second operating mode comprises one of the implantable medical device providing no stimulation or sensing, the implantable medical device providing stimulation but no sensing, or the implantable medical device providing sensing but no stimulation.

27. The device of claim 19, wherein the disruptive energy field comprises one of a magnetic field, an electric field and an electromagnetic field.

28. A non-transitory computer-readable medium comprising instructions that, when executed, cause an implantable medical device to:
configure the implantable medical device from a first operating mode to a second operating mode that is less susceptible to undesirable operation in a disruptive energy field than the first operating mode;
set a timing mechanism to track an amount of time that has elapsed since configuring the implantable medical device from the first operating mode to the second operating mode;
monitor for presence of the disruptive energy field;
automatically configure the implantable medical device from the second operating mode to the first operating mode when (i) the amount of time that has elapsed since configuring the implantable medical device from the first operating mode to the second operating mode exceeds a threshold amount of time, wherein the threshold amount of time is not equal to zero and (ii) the disruptive energy field was detected before the amount of time exceeds the threshold amount of time and the disruptive energy field is not currently detected; and
continue to operate the implantable medical device in accordance with the second operating mode when condition (i) is met and no disruptive energy field is detected between when the implantable medical device is configured from the first operating mode to the second operating mode and when condition (i) is met.

29. The non-transitory computer-readable medium of claim 28, wherein the threshold amount of time is a first threshold amount of time, the non-transitory computer-readable medium further comprising instructions that, when executed, cause the implantable medical device to:
track an amount of time since the disruptive energy field was last detected;
continue to operate the implantable medical device in accordance with the second operating mode even when conditions (i) and (ii) are met when the amount of time since the disruptive energy field was last detected is less than a second threshold amount of time; and
configure the implantable medical device from the second operating mode to the first operating mode when the amount of time since the disruptive energy field was last detected is greater than or equal to the second threshold amount of time.

30. An implantable medical device comprising:
a processor programmed to configure the implantable medical device from a first operating mode to a second operating mode that is less susceptible to undesirable operation in a disruptive energy field than the first operating mode;
a first timing mechanism to track an amount of time that has elapsed since configuring the implantable medical device from the first operating mode to the second operating mode;
a disruptive field detector to monitor for presence of the disruptive energy field;
a second timing mechanism to track an amount of time since the disruptive energy field was last detected, wherein:
the processor is programmed to automatically configure the implantable medical device from the second operating mode to the first operating mode when (i) the amount of time that has elapsed since configuring the implantable medical device from the first operating mode to the second operating mode exceeds a threshold amount of time and (ii) the disruptive energy field was detected before the amount of time exceeds the threshold amount of time and the disruptive energy field is not currently detected,
the processor is further programmed to continue to operate the implantable medical device in accordance with the second operating mode even when conditions (i) and (ii) are met when the amount of time tracked by the second timing mechanism is less than a second threshold amount of time.

31. The device of claim 30, wherein the processor is further programmed to configure the implantable medical device from the second operating mode to the first operating mode when the amount of time since the disruptive energy field was last detected is greater than or equal to the second threshold amount of time.

* * * * *